(12) United States Patent
Sarchese et al.

(10) Patent No.: US 6,507,028 B2
(45) Date of Patent: Jan. 14, 2003

(54) RADIATION SOURCE MODULE

(75) Inventors: Michael P. Sarchese, Belmont (CA); Frank A. Stauder, London (CA)

(73) Assignee: Trojan Technologies, Inc. (CA)

( * ) Notice: Subject to any disclaimer, the term of this patent is extended or adjusted under 35 U.S.C. 154(b) by 0 days.

(21) Appl. No.: 09/736,244

(22) Filed: Dec. 15, 2000

(65) Prior Publication Data

US 2002/0190220 A1 Dec. 19, 2002

Related U.S. Application Data

(60) Provisional application No. 60/172,158, filed on Dec. 17, 1999, and provisional application No. 60/194,040, filed on Apr. 3, 2000.

(51) Int. Cl.$^7$ .............................................. G01N 21/51
(52) U.S. Cl. ................... 250/436; 422/186; 422/186.3; 422/186.07
(58) Field of Search ................ 250/436, 435, 250/432 R, 504 R; 422/243, 24, 121, 186, 186.3, 186.07

(56) References Cited

U.S. PATENT DOCUMENTS

| 4,482,809 A | 11/1984 | Maarschalkerweerd ..... 250/436 |
| 4,752,401 A * | 6/1988 | Bodenstein ................. 250/436 |
| 4,872,980 A | 10/1989 | Maarschalkerweerd ..... 210/243 |
| 5,006,244 A | 4/1991 | Maarschalkerweerd ..... 210/243 |
| 5,019,256 A | 5/1991 | Ifill et al. .................... 210/232 |
| 5,368,826 A * | 11/1994 | Weltz et al. ................ 250/436 |
| 5,418,370 A | 5/1995 | Maarschalkerweerd ..... 250/431 |
| 5,471,063 A * | 11/1995 | Hayes et al. ................ 250/436 |
| 5,539,209 A | 7/1996 | Maarschalkerweerd ..... 250/431 |
| 5,539,210 A | 7/1996 | Maarschalkerweerd ..... 250/372 |
| 5,590,390 A | 12/1996 | Maarschalkerweerd .. 422/186.3 |
| 5,660,719 A | 8/1997 | Kurtz et al. .................. 210/85 |
| 5,894,130 A * | 4/1999 | Bach .......................... 250/436 |
| 6,193,939 B1 | 2/2001 | Kozlowski ............... 422/186.3 |
| 6,201,355 B1 * | 3/2001 | Morgan et al. ............. 250/436 |
| 6,231,820 B1 | 5/2001 | Wedekamp ............. 422/186.3 |

FOREIGN PATENT DOCUMENTS

| DE | 41 19 725 A1 | 1/1993 |
| DE | 196 53 083 A1 | 6/1998 |
| WO | WO 00/75080 A1 | 12/2000 |

* cited by examiner

*Primary Examiner*—Kiet T. Nguyen
(74) *Attorney, Agent, or Firm*—Katten Muchin Zavis Rosenman

(57) ABSTRACT

There is disclosed an improved radiation source module having a power supply adapted to be at least partially immersed in a fluid being treated. In one embodiment, the power supply is partly immersed in the fluid being treated. In another embodiment, the power supply is fully submersible in the fluid being treated. A fluid treatment system comprising the radiation source module is also described.

21 Claims, 17 Drawing Sheets

RADIATION SOURCE MODULE

BACKGROUND OF THE INVENTION

1. Field of the Invention

Generally, the present invention relates to radiation source module and to a fluid treatment system incorporating a radiation source module.

2. Description of the Prior Art

Ultraviolet light radiation systems used in applications such as water disinfection are well known in municipal, industrial and domestic applications. Typically, such systems rely on ultraviolet lamps as a source of radiation.

Ultraviolet lamps normally require a power supply (sometimes referred to as a ballast) connected between the lamp and a main source of electricity in order to transform, regulate and/or control the electrical energy supplied to the lamp. Conventionally, power supplies in these applications, whether electronic or electromagnetic, require mounting in a dry location, protected from water or moisture. It is also known that these conventional power supplies dissipate a portion of transformed energy as waste heat that results in an increase in the temperature of the power supply components. Further, ambient conditions surrounding the power supply can result in higher operating temperatures for the power supply components.

Since excessively high temperatures shorten the lifetime of the power supply and/or can cause sudden catastrophic failure, it is normally necessary for the system designed to incorporate a means for removing waste heat and limiting the impact of hot ambient environments.

Ultraviolet systems which require relatively low power lamps normally can adequately dissipate the waste heat from the power supplies via natural convection of the ambient air environment in which they are used. Examples of such systems may be found in:

U.S. Pat. No. 4,482,809;
U.S. Pat. No. 4,872,980; and
U.S. Pat. No. 5,006,244.

In recent years, significant interest has been expressed in the use of higher power-lamps in ultraviolet radiation systems. These higher power lamps normally require either large cabinets with forced air cooling to house the power supplies and/or complex arrangements for forced air and/or cooling liquid if the power supplies are to be housed in more compact enclosures. See, for example, any of the following:

U.S. Pat. No. 5,418,370;
U.S. Pat. No. 5,539,210; and
U.S. Pat. 5,590,390 (Re.36,896).

The need to use large cabinets to house the power supplies renders it difficult to install such systems in a small area. Further, the capital costs of the system increase. Still further, air flow into and out of these cabinets is often hindered by blocked filters, necessitating additional maintenance. Still further, if forced liquid cooling is used, the capital costs and complexity of the system increases.

Additionally, further complexity and expense is associated with the above systems in that individual conductors must be used to carry electrical power over the relatively long distance from the power supply to the lamp. The problems associated with these relatively long conductors becomes more difficult to solve when higher frequency alternating current is used to operate the lamps.

It would be desirable to have a radiation source module which could be used in a fluid treatment system to overcome one or more of the above-identified disadvantages of the prior art.

SUMMARY OF THE INVENTION

It is an object of the present invention to provide a novel radiation source module which obviates or mitigates at least one of the above-mentioned disadvantages of the prior art.

It is another object of the invention to provide a fluid treatment system which obviates or mitigates at least one of the above-identified disadvantages of the prior art.

Accordingly, in one of its aspects, the present invention provides a radiation source module comprising a frame having a first support member, at least one radiation source assembly extending from and in engagement with the first support member, a radiation source disposed in the radiation source assembly, connection means for affixing the radiation source module in a fluid treatment system and a power supply connected to the frame and adapted to be in contact with a fluid.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Figure 1:
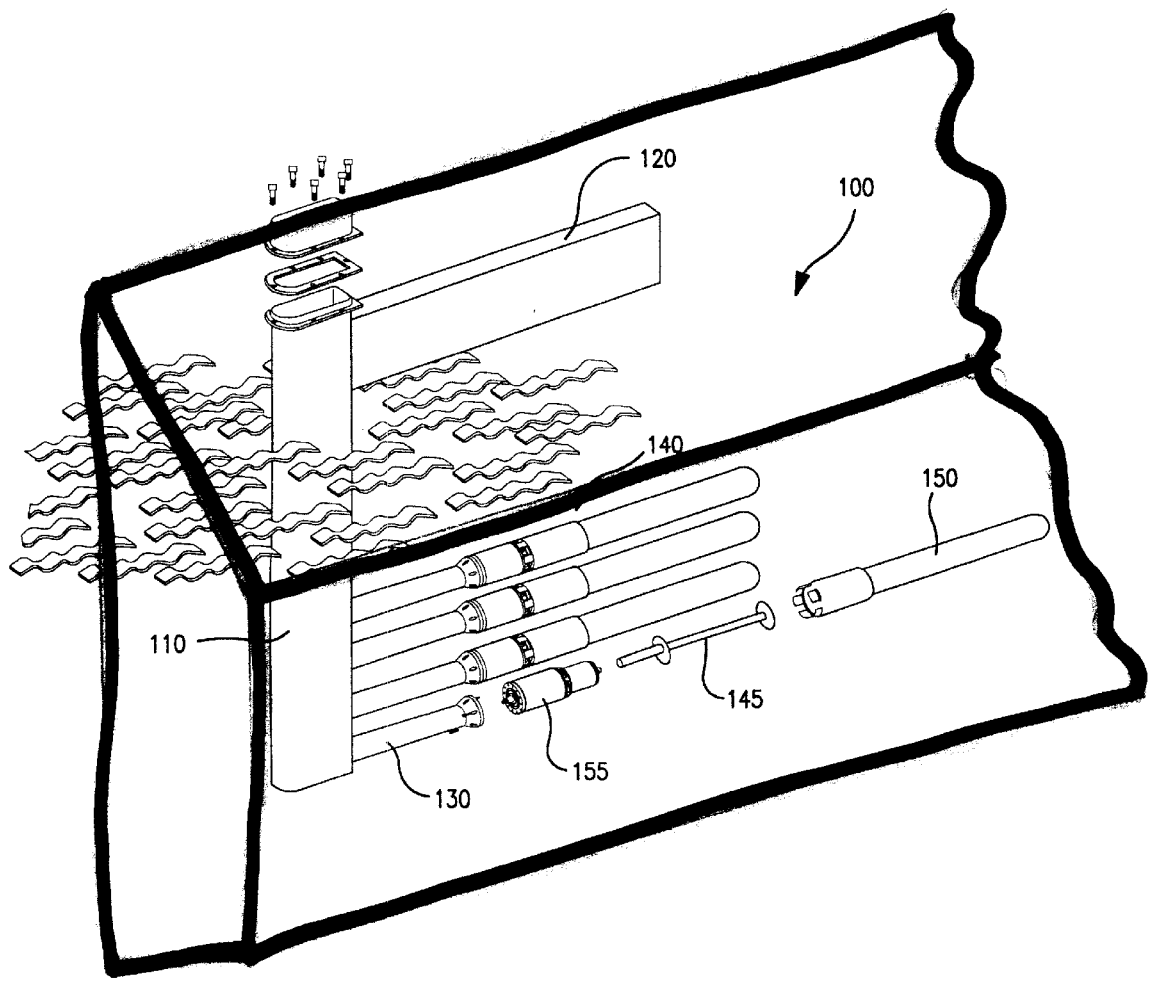
FIGS. 1–17 illustrate various embodiments of the present invention.

Thus, the present invention relates to a novel arrangement of power supplies used for radiation source modules in order to obviate or mitigate the above-mentioned problems of the prior art while the invention will be described with reference to ultraviolet radiation source modules and fluid treatment systems incorporating such modules, those with skill in the art that will recognise that the invention can be used in connection with a radiation source generally and in connection with various fluids including liquids and gases.

The preferred embodiment of the present invention is to dispose the power supply or supplies in the radiation source module such that it is submerged in the fluid being treated by the radiation sources in the radiation source module. This provides a relatively high capacity cooling medium for the power supply facilitating the use of higher power radiation sources. This arrangement also can eliminate the need for larger enclosures to house the power supply. A further advantage of this arrangement is that the power supply or supplies can be located in closer proximity to the radiation sources thereby minimizing the length of conductors between the radiation sources and the power supply.

An alternate embodiment of the invention is to dispose the power supply or supplies in a contained fluid preferably a liquid) which is remote from the fluid being treated. This arrangement may be useful in circumstances where the fluid being treated is not suitable for immersion of the power supply. Yet a further embodiment relates to a system in which the power supply is immersed in a fluid, and the radiant energy from the radiation source is used to irradiate a gas or mixture of gases for the purposes of treating contaminants therein. A practical example where this could be desirable is where air stripping is used to remove contaminants from water and then the contaminant laden air is irradiated. In this example, there is a readily available water source in which the power supply may be immersed to provide adequate cooling without the need for additional enclosures or cooling apparatus.

Another embodiment of the invention relates to a design wherein a portion of the power supply is partly immersed in the fluid being treated to facilitate waste heat dissipation.

FIGS. 1–17 illustrate various embodiments of the present invention. Accompanying each Figure is text which provides further detail concerning each embodiment.

Generally, the embodiment illustrated in FIGS. 1–10 relates to a radiation source module which may be used in a fluid treatment system such as the one illustrated in U.S. Pat. No. 5,590,390. As illustrated, a power supply (ballast) is disposed between an extension from the support leg and the quartz sleeve, lamp combination. The components may be connected via a combination of fasteners (e.g., screws, etc.) and/or snap-connectors. In the illustrated embodiment, the ballast is shown to be fully fluid submersible. Further, in the illustrated embodiment, a single ballast is provided for each lamp assembly. As will be apparent to those of skill in the art, waste heat which is generated by the ballast is simply dissipated in the fluid being treated Further, the length of conductor needed to convey electricity to the ballast from the source of electricity is relatively short. In FIGS. 5–10, further detail is provided on how the ballast is installed in the module and a sealing arrangement is described to prevent ingress of fluid into the ballast area from either the support leg side or the lamp, protective sleeve side. The specific components within the ballast are shown generally only as these are conventional and within the purview of a person skilled in the art In a preferred embodiment, the power conversion device is housed in a sealed chamber which comprise a heat conducting, dielectric fluid to facilitate cooling—see FIGS. 9 and 11.

With reference to FIG. 1, there is illustrated a radiation source module 100 which comprises a support member 110. Connected to support member 110 is a connection bar 120. Emanating from support member 110 are four support arms 130. A radiation source assembly 140 is provided and comprises a radiation lamp 145 disposed within a radiation transparent protective sleeve 150. A power supply 155 is interposed between each support arm 130 and each radiation source assembly 140 in a fluid tight manner.

Figure 2:
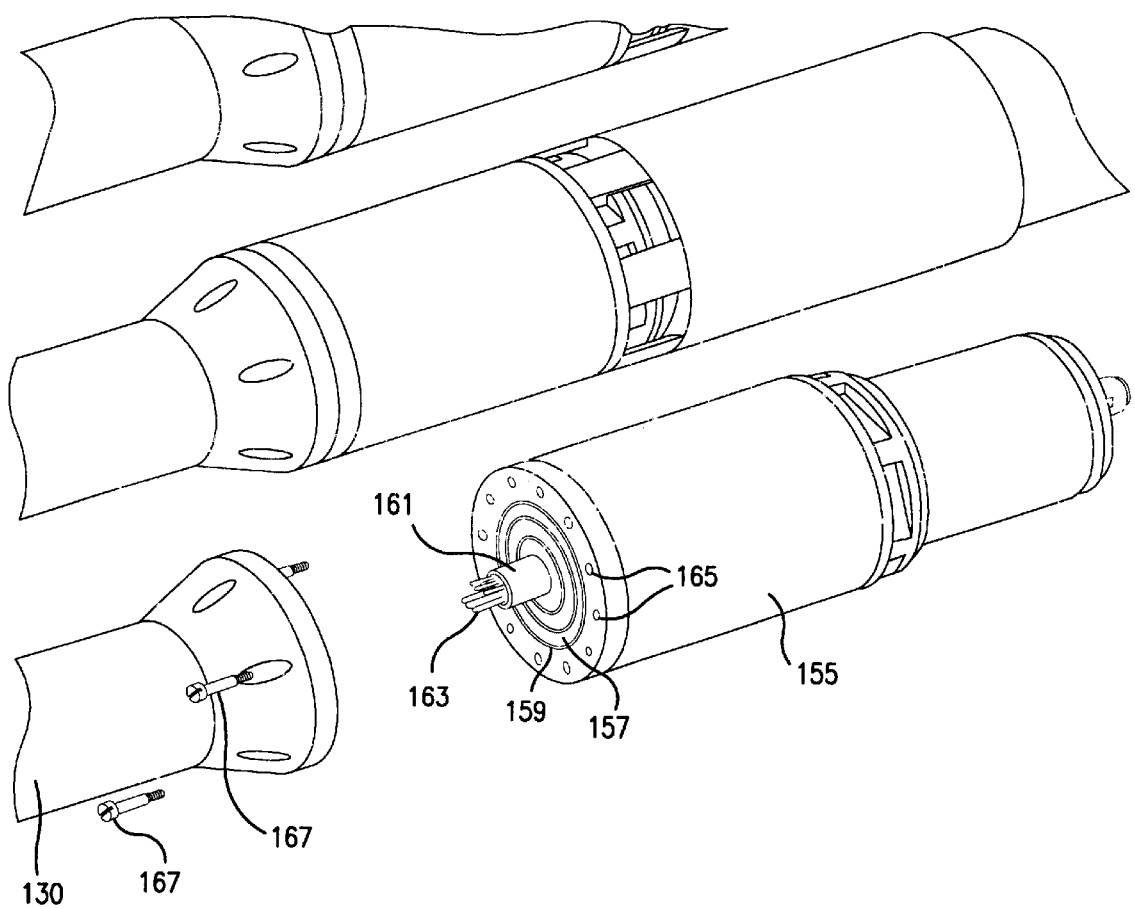
Figure 3:
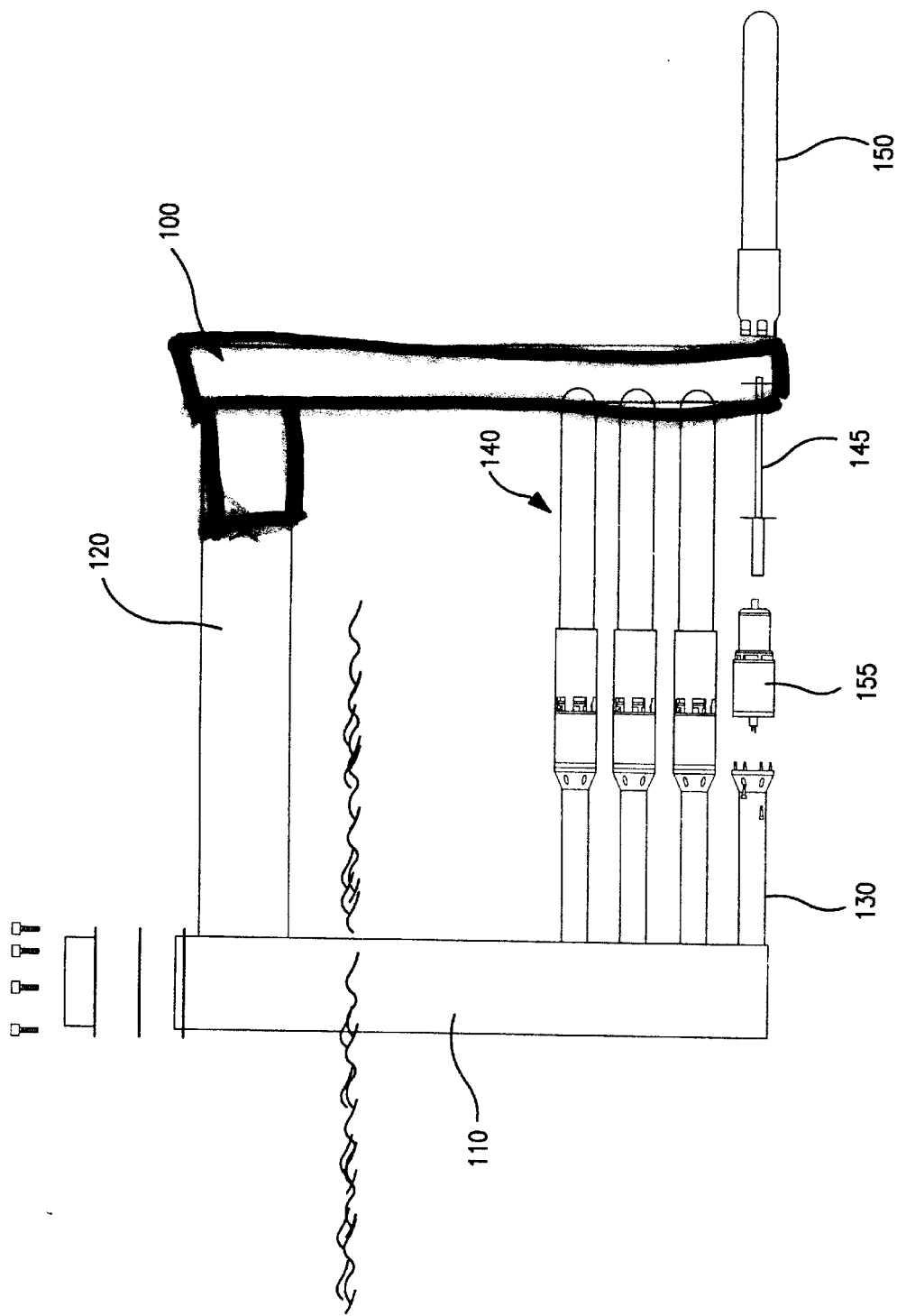
Figure 4:
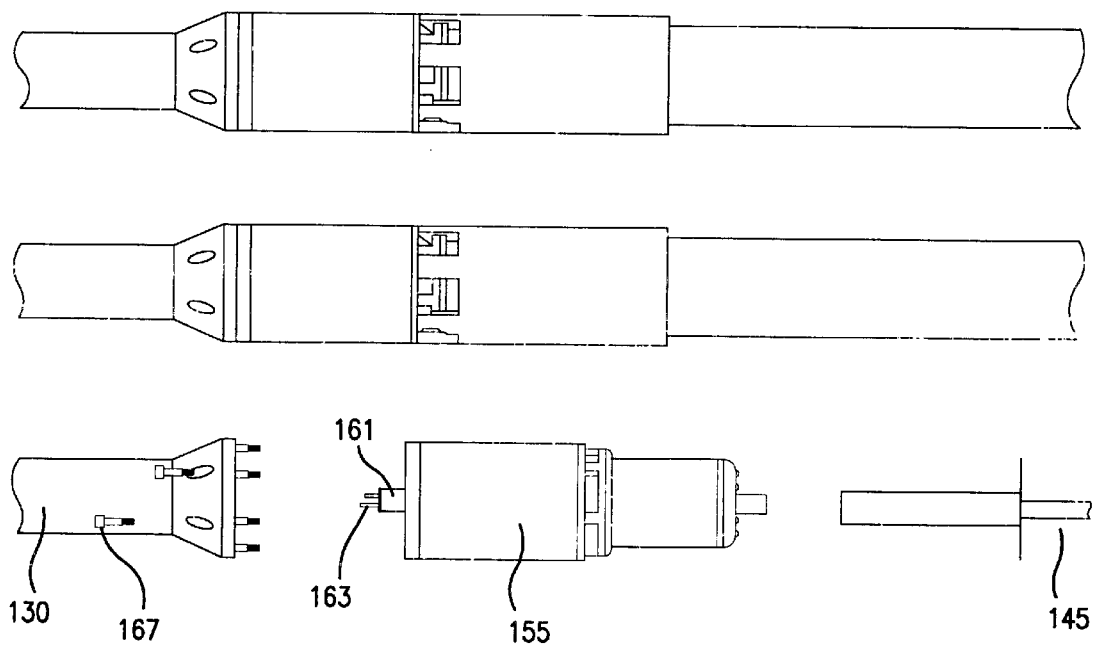

With reference to FIG. 2, there is illustrated an enlarged portion of power supply 155 in FIG. 1. Thus, power supply 155 comprises a pair of O-rings 157,159. Emanating from the proximal end of power supply 155 is an electrical plug 161 comprising a series of pins 163. A number of threaded appatures 165 are also provided on the proximal side of power supply 155. A series of screws 167 are passed through support arm 130 and engage threaded apertures 165 of power supply 155 in a fluid tight manner.

Figure 5:
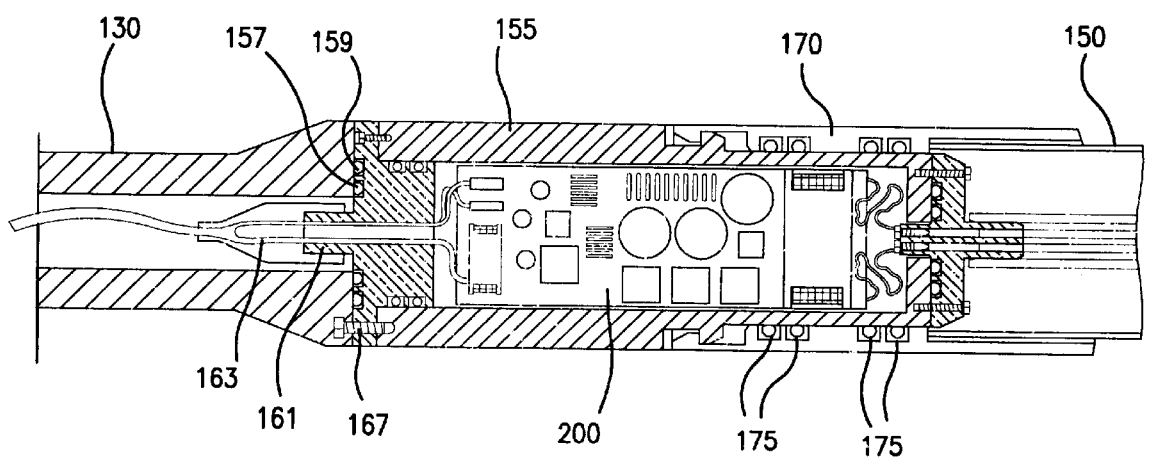

FIG. 5 illustrates a sectional view of preferred embodiment of power supply 155 and how it is connected to support arm 130 and protective sleeve 150 of radiation source assembly 140.

As illustrated, a sleeve holder 170 is attached to protective sleeve 150. Sleeve holder 170 is capable of biassing away from the longitudinal axis of protective sleeve 150. As will be understood by those of skill in the art, this biassing action, in combination with a series of O-rings 175, serves to provide a fluid tight seal between sleeve holder 170 and power supply 150. Disposed within power supply 155 is a circuit board 200 comprising electrical components of the power supply 155.

Figure 6:
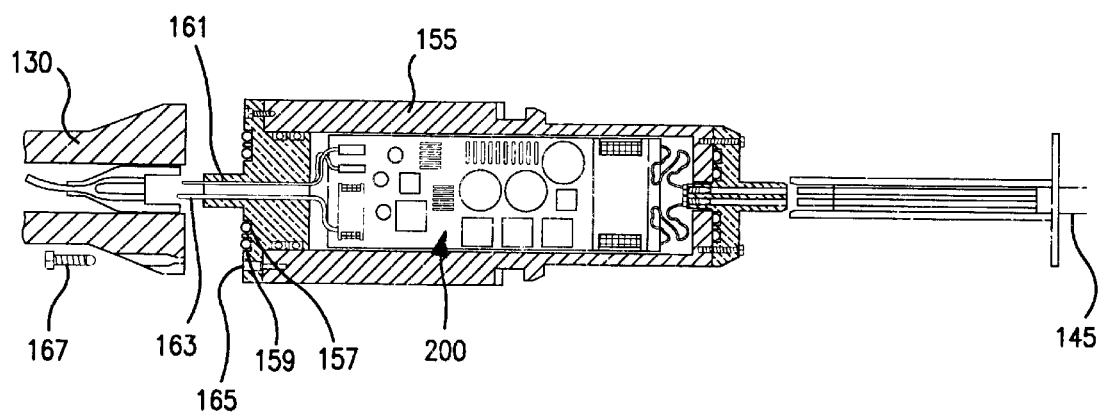
Figure 7:
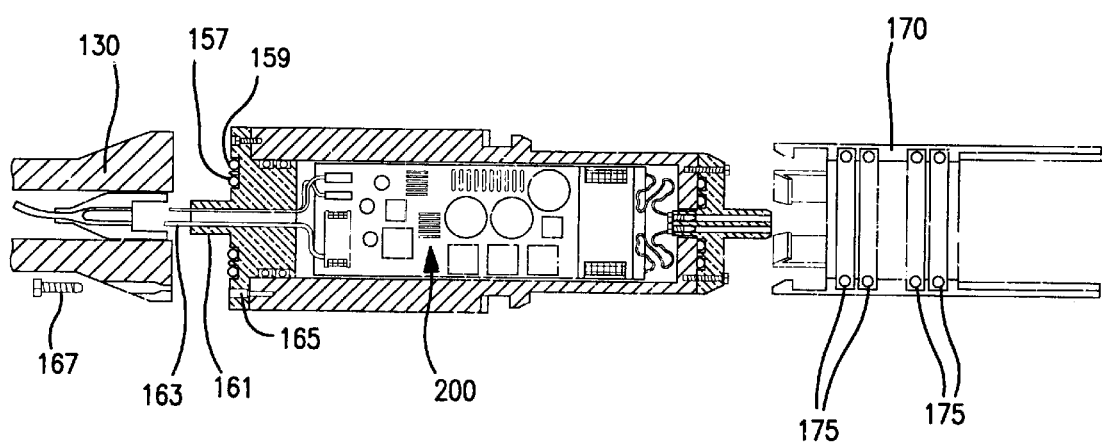
Figure 8:
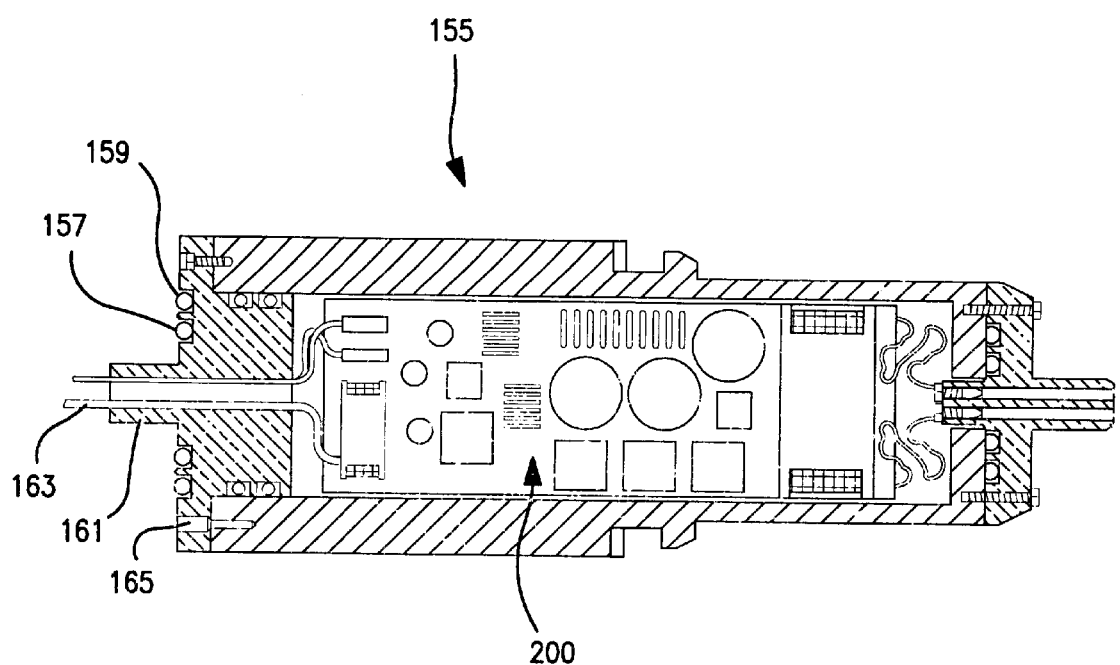

FIGS. 6–8 illustrate various other views of power supply 155.

Figure 9:
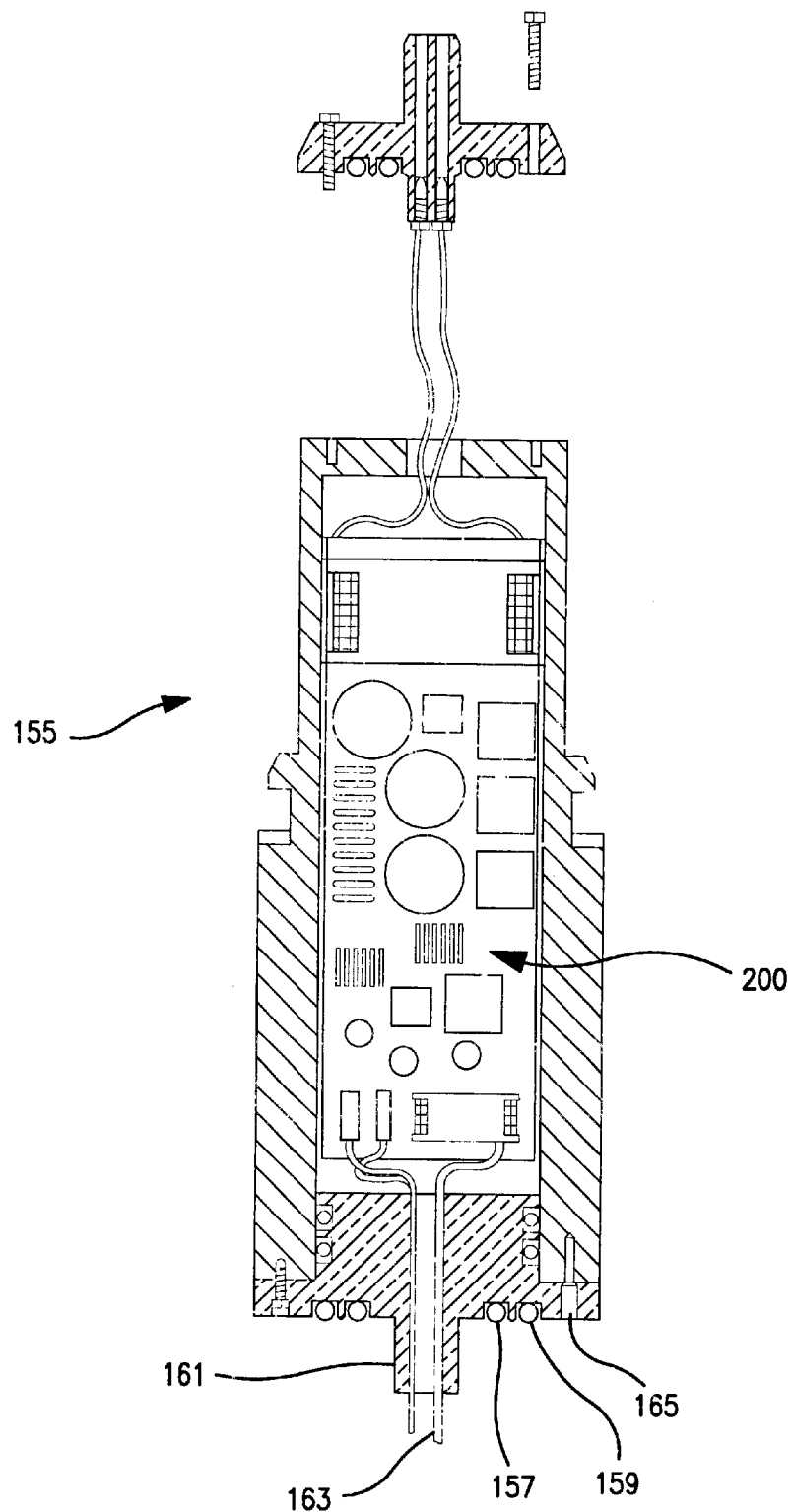
Figure 10:
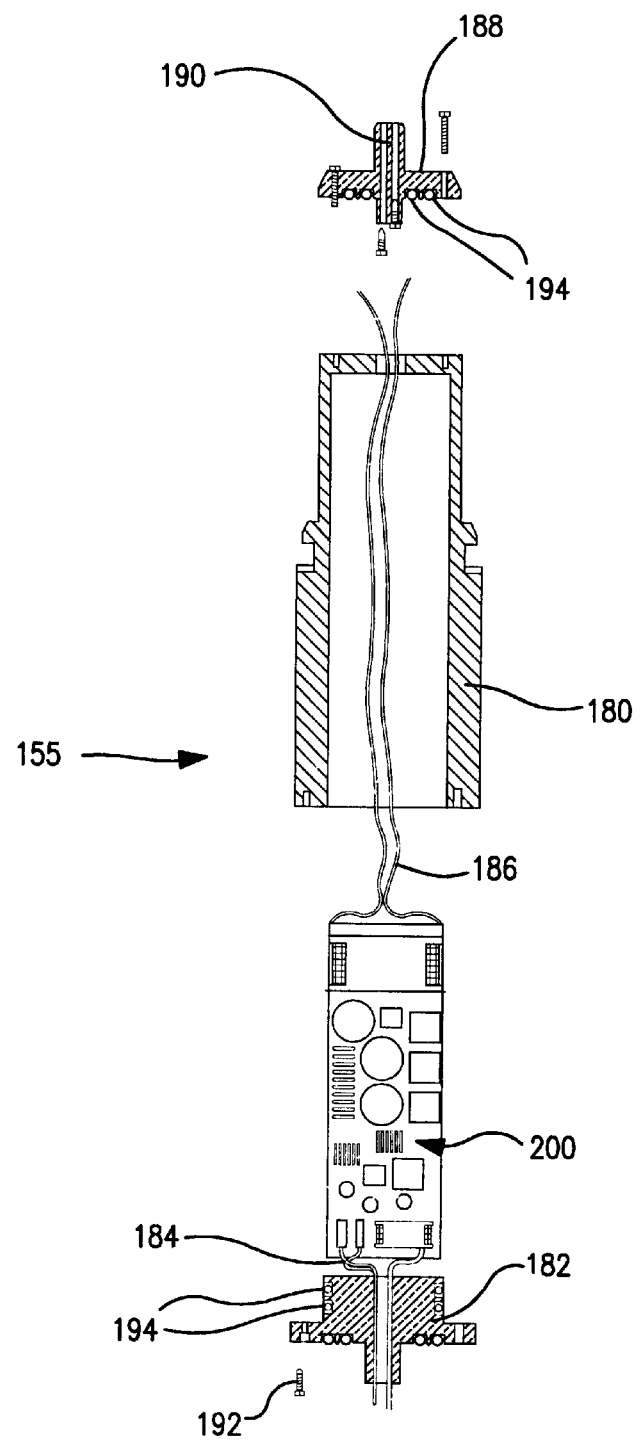

FIGS. 9–10 illustrate construction of power supply 155. Thus, there is illustrated a ballast shell 180. Circuit board 200 is connected to a first end-cap 182 via electrical connections 184. Opposed to this are lamp leads 186 which are connected to a second end-cap 188 comprising receptacles 190 for connection to lamp 145. First end-cap 182 and second end-cap 188 are connected to ballast shell 180 via the series of screws 192 which, in combination with O-rings 194 serve to provide a fluid tight seal to obviate or mitigate fluid ingress to circuit board 200 within ballast shell 180.

Figure 11:
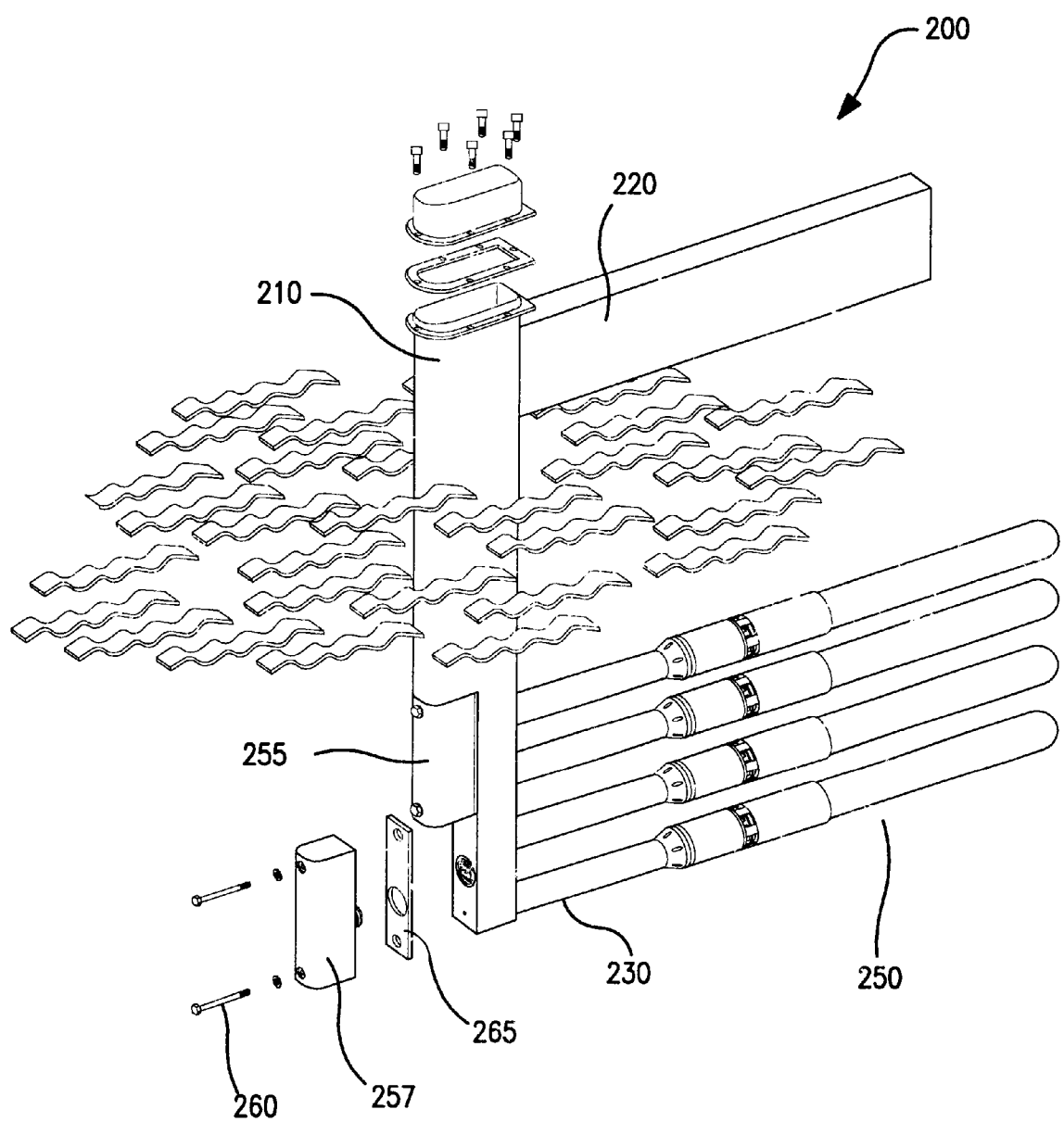
Figure 12:
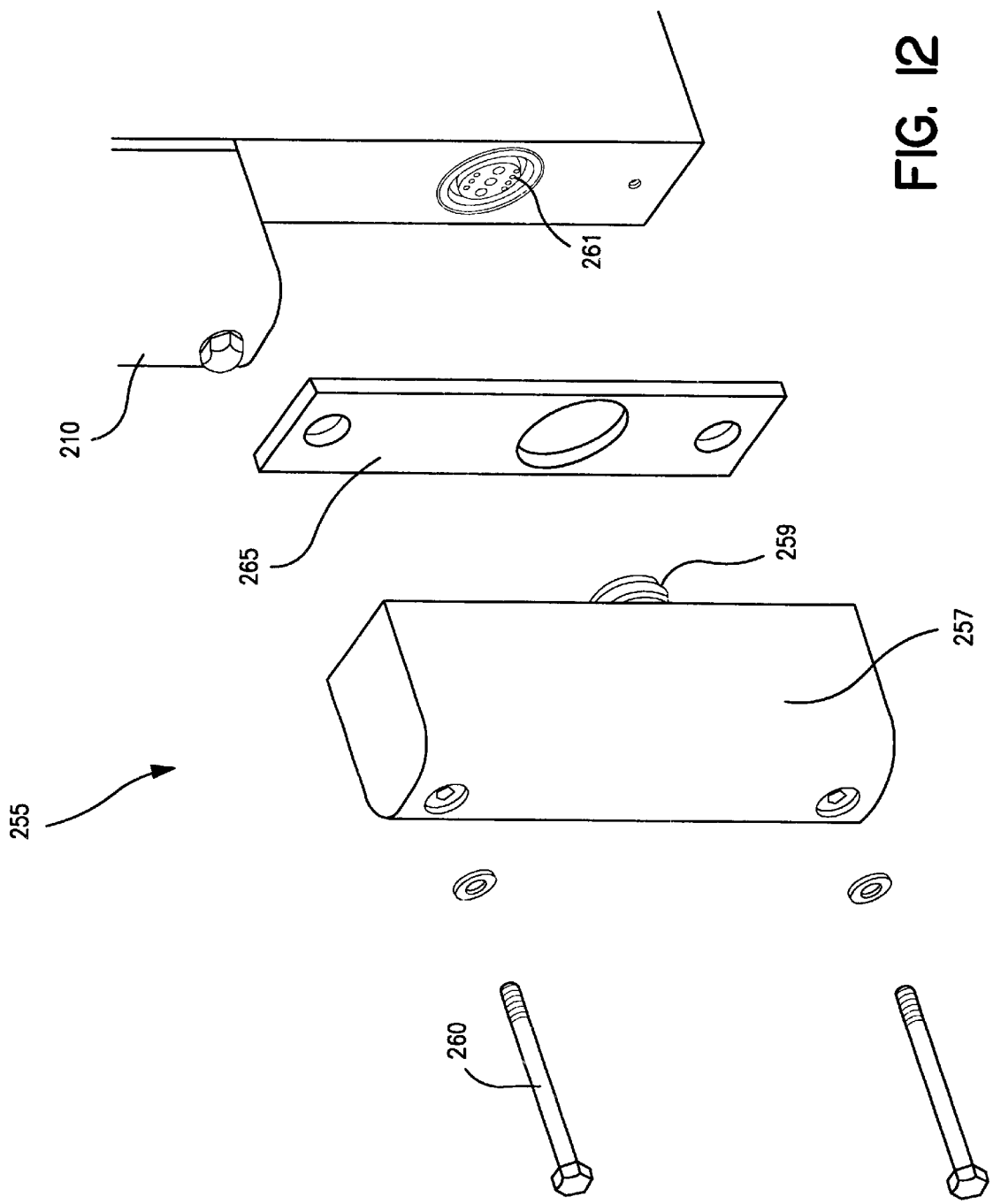
Figure 13:
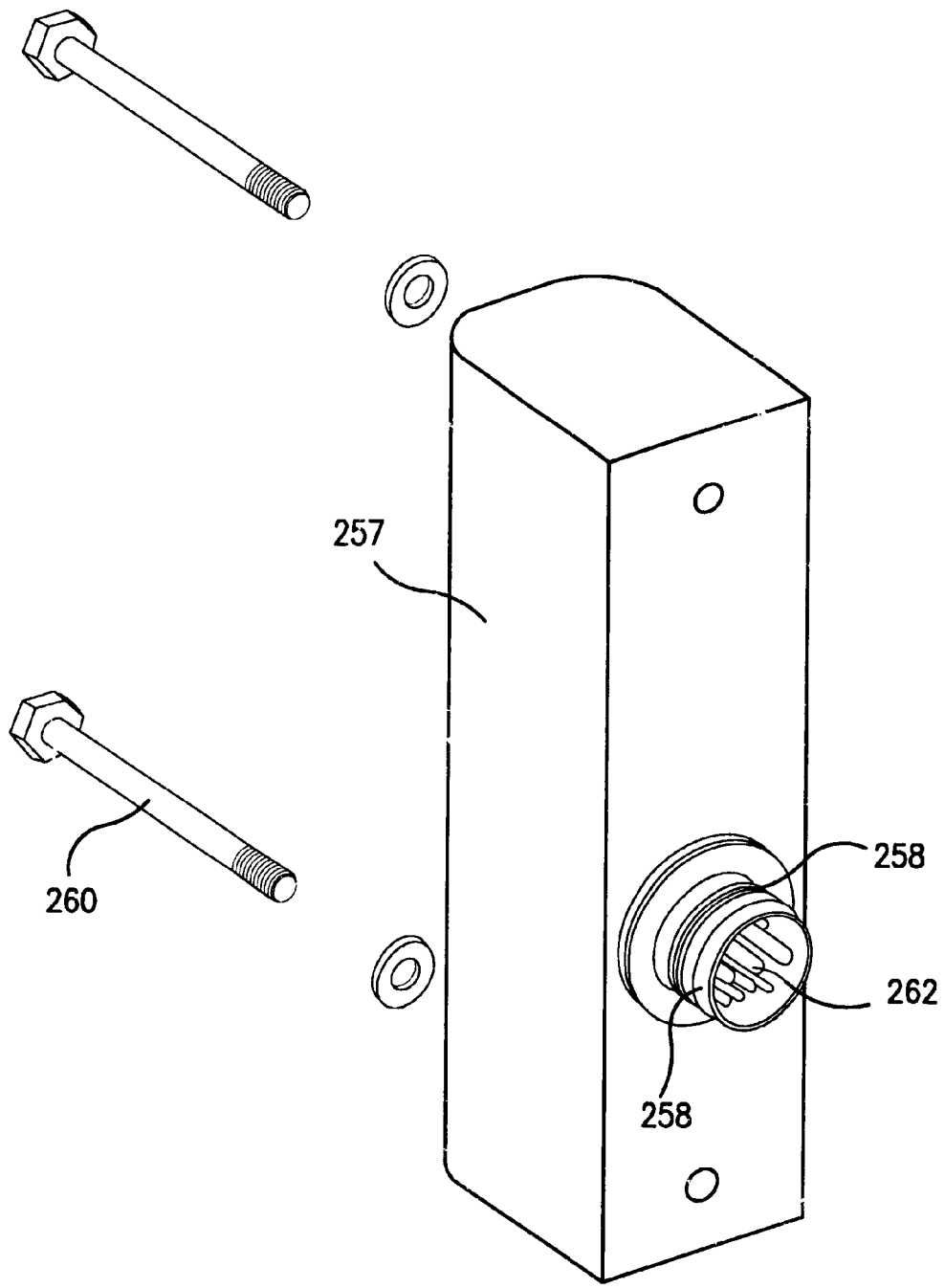

In FIGS. 11–13, there is illustrated and alternative embodiment of the present radiation source module. Again, the module illustrated in FIGS. 11–13 may be used in a fluid treatment system such as the one described in U.S. Pat. No. 5,590,390. In this case, the power supply or ballast is located on a face of the support leg opposed to the face from which the lamp/protective sleeve emerges. As illustrated, one power supply will control a pair of lamps. As will be apparent to those of skill in the art, advantages of the embodiment illustrated in FIGS. 11–13 include simpler sealing mechanisms with respect to mitigating or obviating fluid ingress to the power supply. Further, in order it service the power supply, it is not necessary to break the seal between the quartz sleeve and remainder of the module. The detail of the power supply is similar to the embodiment illustrated in FIGS. 1–10.

With reference to FIG. 11–13, there is illustrated a radiation source module 200 comprising a support member 210 and a connection bar 220. Emanating from support member 210 are four support arms 230. Connected to each support arm 230 is a radiation source assembly 250. On the opposed side of support member 210 are a pair of power supplies 255 each of which comprise a ballast 257 and a gasket 265 which are affixed to support member 210 via screws 260.

With reference to FIGS. 12 and 13, it will be seen that power supply 255 comprises a ballast 257 having a male electrical connector 259. Male electrical connector 259 engages a female electrical connector 261 on support member 210.

FIG. 13 illustrates various components of FIG. 12 from a different view. As shown, connector 259 comprises an O-ring 258 and a series of electrical contact pins 262.

Figure 14:
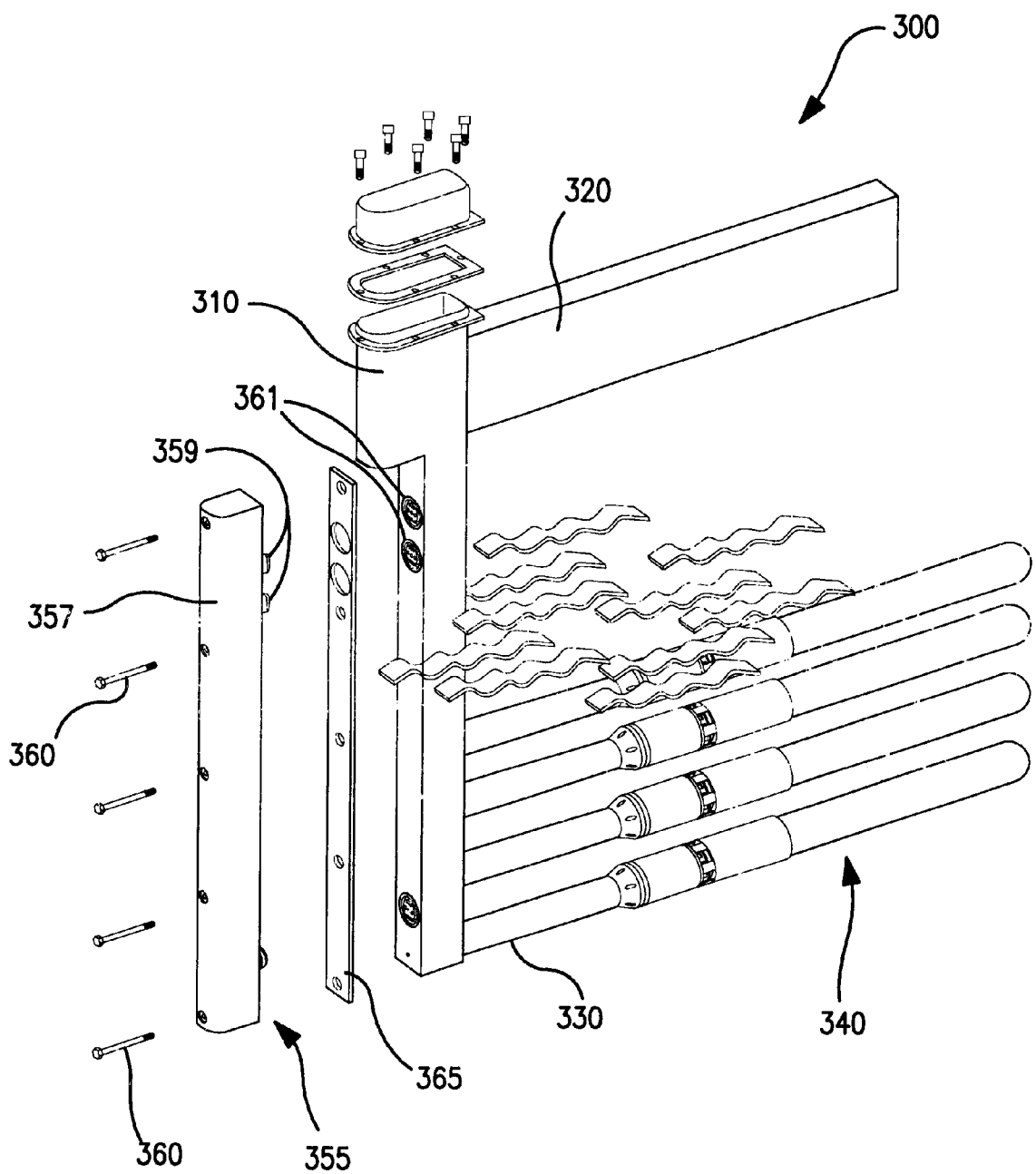

With reference to FIG. 14, there is illustrated yet a further modification to the present radiation source module. Specifically, the power supply is in the form of bar which is secured to the support leg in the module at a face opposite to the face from which the lamp/protective sleeve extend. As shown, the electrical connections between the support leg and the power supply are above the water level thereby further facilitating keeping the internal circuitry of the power supply dry with respect to mitigating or obviating fluid ingress to the power supply. Further, in order to service the power supply, it is not necessary to break the seal between the quartz sleeve and remainder of the module.

With reference to FIG. 14, there is a illustrated a further embodiment of the present radiation source module. Thus, there is illustrated a radiation source module 300 comprising a support member 310 and a connection arm 320. Emanating from support member 310 are four support arms 330 which are connected to respective radiation source assembly 340. On the opposite side of support member 310 is an elongate power supply 355 comprising a ballast 357 and a gasket 365 which are attached to support member 310 via a series of screws 360. Ballast 357 has a pair of male electrical connection plugs 359 which engage a pair of female electrical connector plugs 261 on support member 310.

Figure 15:
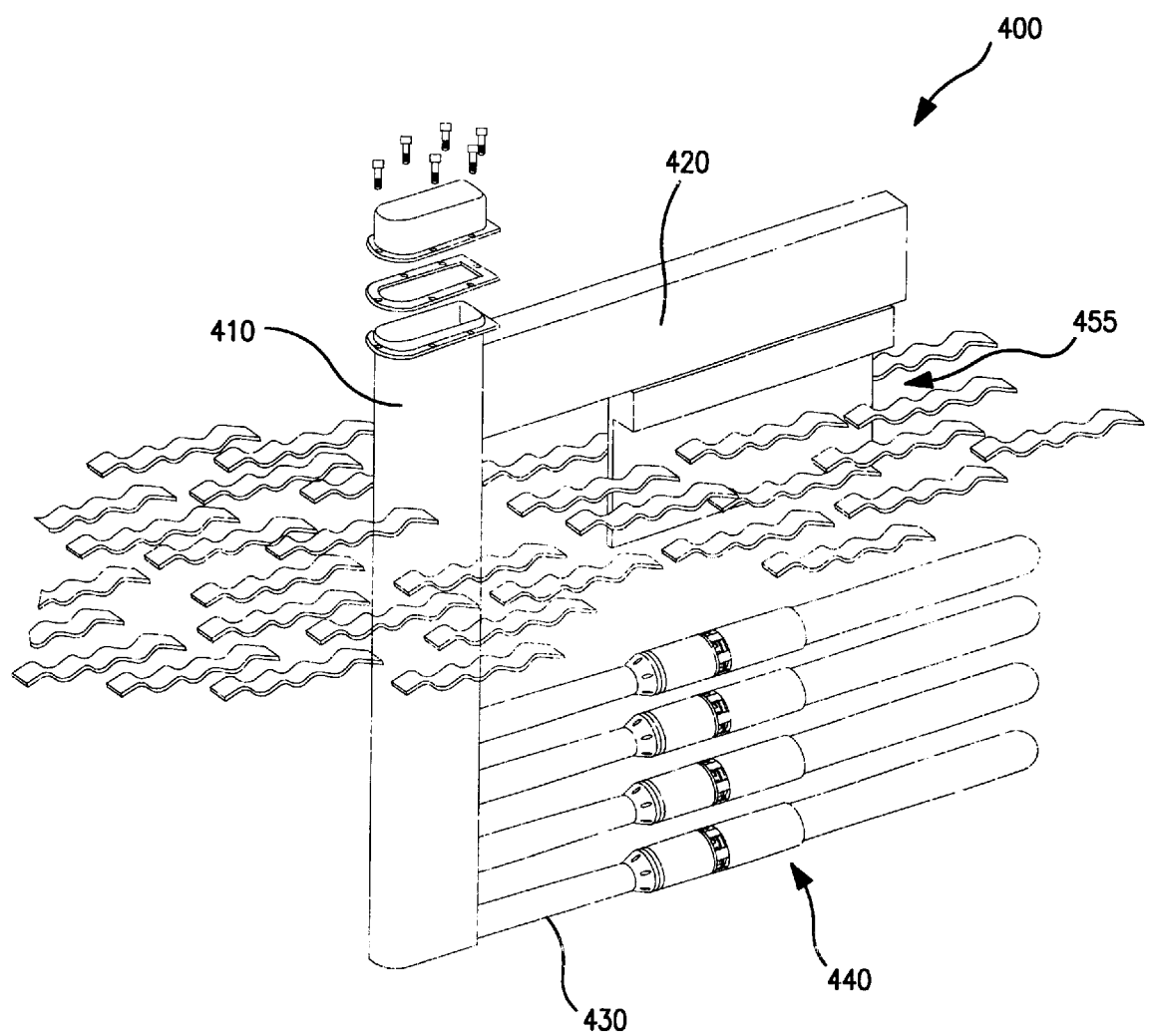
Figure 16:
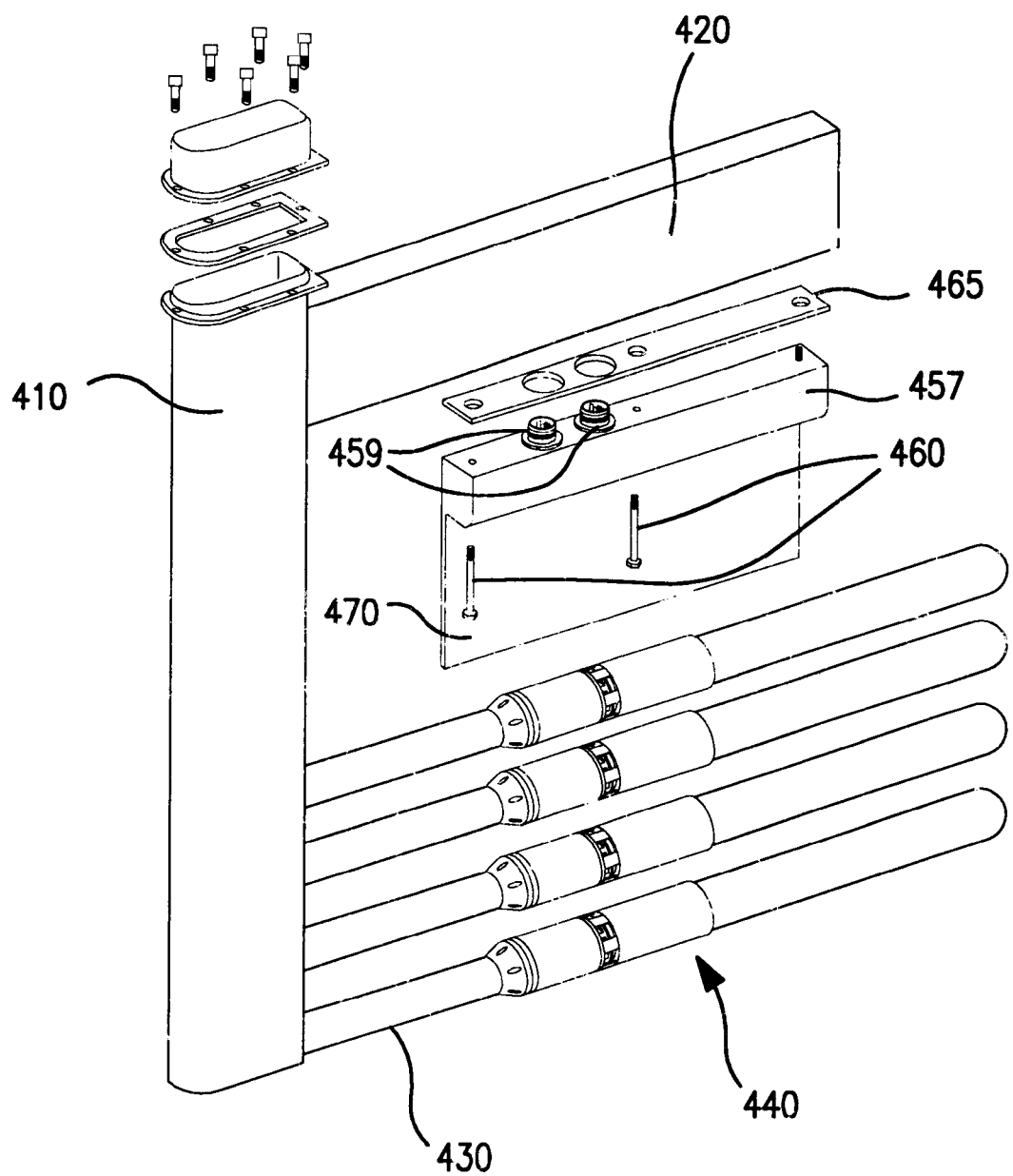
Figure 17:
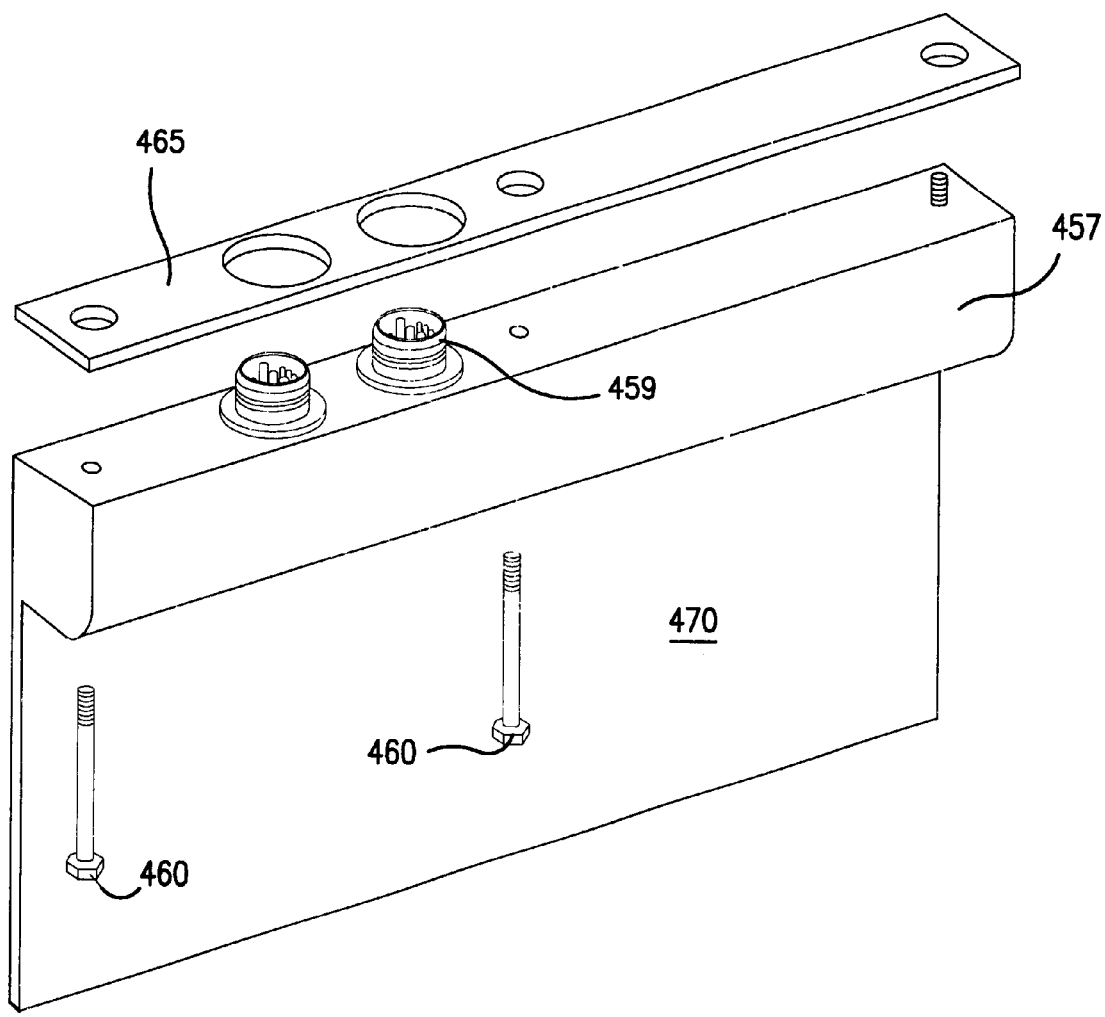

In FIGS. 15–17 yet a further modification is illustrated. In his case, the circuitry of the power supply is attached to a portion of the module which is outside the fluid being treated At least a portion of the power supply housing is heat conducting and this portion is in contact with or at least partially immersed in the fluid being treated. For example, as illustrated, a heat conductive "fin" may extend from the power supply housing into the fluid being treated thereby facilitating dissipation of heat generated by the power supply. While a particular "fin" profile is illustrated, those of skill in the art will immediately recognize that the particular shape of the "fin" profile is not restricted.

With reference to FIGS. 15–17, there is illustrated another embodiment of the present radiation source module. Thus, there is illustrated a radiation source module 400 comprising a support member 410 and a connection bar 420. Emanating from support member 410 are four support arms 430. Each support arm 430 is connected to a radiation source assembly 440. Depending from connection bar 420 is a power supply 455. Power supply 455 comprises a ballast 457 and a gasket 465 which are connected to connection bar 420 via a series of screws 460. Ballast 457 comprises a pair of male electrical connectors 459 which engage with a pair of female electrical connectors (not shown) in connecting arm 420. Depending downwardly from ballast 457 is a cooling fin 470. In one embodiment, cooling fin 470 may be a solid heat conductive material which will serve to convey heat generated from the ballast to the fluid being treated (i.e., the fluid acts as a heat sink). In another embodiment, a fin may be hollow and, optionally, filled with a cooling fluid to assist in heat transfer from the ballast to the fluid being treated.

While the present invention has been described with reference to preferred and specifically illustrated embodiments, it will of course be understood by those skilled in the art that various modifications to these preferred embodiments and illustrated embodiments may be made without departing from the spirit and scope of the invention. For example, while present radiation source module has been illustrated with reference to a module suitable for use in the fluid treatment system described in U.S. Pat. No. 5,590,390, those with skill in the art will readily appreciate that the present invention could be applied readily to a "double-legged" module similar to the ones illustrated in U.S. Pat. Nos. 4,482,809, 4,872,980 and 5,006,244. Still further, with reference to the embodiments illustrated in FIGS. 1–14, it is possible to modify the power supply shell to include projecting fins (not shown) which would serve to facilitate heat dissipation and create mixing thereby improving efficiency of fluid treatment in the radiation zone. Still further, while various of the embodiments specifically described hereinabove with reference to the drawings relate to the use of a power supply conventionally used to power ultraviolet radiation sources—e.g., low frequency AC (50 Hz to 500 kHz) power supplies—those of skill in the art will readily appreciate that alternate power supplies may be used with the present radiation source module without departing from the spirit and scope of the invention. For example, any of the following alternate power supplies may be used in the present radiation source module: a direct current power supply, other high radio frequency power supplies or a microwave excitation power supply. The present invention is particularly applicable in respect of the latter two alternate power supplies where efficiency improvements and reductions of electromagnetic interference are seen as the power supply and radiation source are moved in closer proximity to one another. Still further, while various of the embodiments specifically described hereinabove with reference to the drawings relate to direct immersion or submersion of the power supply resulting in direct heat exchange between the power supply and the fluid being treated, those of skill in the art will immediately recognize that the power supply may be encased in another structure (e.g., the support leg for the radiation source) which is directly in contact with the fluid to provide heat exchange with the fluid being treated thereby obtaining the benefits of the invention without departing from the spirit or scope thereof. Other modifications which do not depart from the spirit and scope of the present invention will be apparent to those of skill in the art.

All publications, patents and patent applications referred to herein are incorporated by reference in their entirety to the same extent as if each individual publication, patent or patent application was specifically and individually indicated to be incorporated by reference in its entirety.

LEGEND OP THE FIGURES

| Figure | Description |
| --- | --- |
| 1 | UV light module with submerged power supply; isometric view |
| 2 | Submerged power supply disconnected from module frame and lamp and sleeve |
| 3 | UV light module with submerged power supply: side view |
| 4 | Submerged power supply disconnected from module frame and lamp and sleeve |
| 5 | Sealed power supply shown secured and sealed to the module frame member (left). A plug conveying electrical input power and status/control signals is connected to the power supply at left.<br>The sleeve holder is secured to the power supply case via releasable tabs that engage in corresponding slots. O-rings seal the sleeve holder against the outer case of the power supply.<br>The plug at right carries electrical power from the power supply to the lamp. |
| 6 | Scaled power supply shown in sectional view prior to being fastened in a secure and sealed manner to module frame member (on left side of drawing).<br>Electrical input to the power supply and control and status signals connect through the plug at left.<br>The plug at right conveys electrical power to the lamp. Note that the sleeve is not shown in this view for purpose of clarity. |
| 7 | At right is shown at the end of the sleeve holder, with o-rings and tabs for sealing and securing the sleeve to the power supply case. Note that the lamp is not shown in this view for purpose of clarity. |
| 8 | Sealed power supply shown assembled in sectional view |
| 9 | Secondary (upper) end-cap is connected to wires after the primary endcap and circuit board are installed.<br>Prior to securing secondary endcap, the power supply cavity may be filled with a suitable heat conducting high dielectric (i.e.; does not conduct electricity) material such as Fluorinert ™ Liquid # FC-40 manufactured by 3M ™<br>Use of heat conducing material as described above improves the transfer of waste heat (generated by the power supply) from the power supply to the case, which in turn transfers the heat to the ambient liquid (typically water). |
| 10 | Primary endcap (lower) is wired to circuit board prior to insertion into case. |
| 11 | UV light module with power supply secured to frame member and submerged beneath liquid surface. Note that in this arrangement it is possible to have more than one lamp operated from a single power supply (shown with one power supply operating two lamps, electrical connections through a single plug).<br>Power supply electronics are completely sealed within watertight case.<br>Internal cavity within power supply case way be filled with a suitable heat conducting high dielectric (i.e.: does not conduct electricity) material such as Fluorinert ™ Liquid # FC-40 manufactured by 3M ™<br>Use of bear conducting material as described above improves the transfer of waste heat (generated by the power supply) from the power supply to the case, which in turn transfers the heat to the ambient liquid (typically water). |
| 12 | Electrical connections for input power, output power to lamps, and control/status signals are achieved via sealing plug.<br>Gasket between module frame member and power supply provides additional seal to prevent water from reaching electrical connections. |

LEGEND OF THE FIGURES

| Figure | Description |
|---|---|
| 13 | Plug connector shown utilizes sealing O-rings to prevent water ingress into the area where electrical contacts mate. Electrical connections for input power, output power to lamps, and control/status signals are achieved via sealing plug. |
| 14 | The power supply case geometry, when secured to the module frame member, can be arranged such that it is substantially submerged beneath the liquid top surface, but the electrical connections are above the liquid top surface. Such an arrangement allows the heat generating components to be cooled by the liquid that substantially surrounds the ballast case, while allowing the electrical connectors to be rated only for appropriate weather resistance and temporary submersion (rather than being rated for continuous submersion). This results in less costly and less complex electrical connection devices. |
| 15 | Power Supply case (with electronic components housed within) shown secured to the module frame member above the top surface level of the liquid. The power supply is substantially above the top surface level of the liquid, but has at least on heat conductive surface in direct contact with the liquid. In the illustration of FIG. 15, a heat conducting fin protrusion extends from the power supply case downward into the liquid. Heat generated by the electronic components is conducted via the fin from the power supply case and discharged into the liquid. This arrangement allows that the power supply case and connections be rated only for appropriate weather resistance and temporary submersion, resulting in less complex and less costly construction. |
| 16 | As FIG. 15, but with power supply detached from module frame member. |
| 17 | Power supply of FIG. 15 and FIG. 16, with heat conductive finned protrusion extending from case. |

What is claimed is:

1. A radiation source module comprising:
a frame having a first support member;
at least one radiation source assembly extending from and in engagement with the first support member;
a radiation source disposed in the radiation source assembly;
connection means for affixing the radiation source module in a fluid treatment system; and
a power supply connected to the frame and configured to be in contact with a fluid, said power supply being connected to said first support member on a side of said first support member which is opposite a side on which said radiation source assembly is connected.

2. The radiation source module defined in claim 1, wherein the fluid comprises fluid being treated.

3. The radiation source module defined in claim 1, wherein the fluid comprises a cooling liquid.

4. The radiation source module defined in claim 3, further comprising a container for the cooling liquid.

5. The radiation source module defined in claim 4, wherein the container is remote from the module.

6. The radiation source module defined in claim 4, wherein the container is attached to the module.

7. The radiation source module defined in claim 6, wherein a portion of the container comprising the cooling liquid is submersible in the fluid being treated.

8. The radiation source module defined in claim 1, wherein the power supply is configured to be fully submersible in a fluid being treated.

9. The radiation source module defined in claim 1, wherein at least one radiation source assembly is cantilevered from the first support member.

10. The radiation source module defined in claim 1, wherein the power supply is interposed between the support member and the radiation source.

11. The radiation source module defined in claim 1, wherein an individual power supply is provided for each radiation source in the module.

12. The radiation source module defined in claim 1, wherein an individual power supply is provided for each pair of radiation sources in the radiation source assembly.

13. The radiation source module defined in claim 1, wherein an individual power supply is provided for a plurality of radiation sources in the radiation source assembly.

14. The radiation source module defined in claim 1, wherein the power supply is connected to the connection means and a portion of the power supply is configured to be immersed in a fluid.

15. The radiation source module defined in claim 1, wherein the frame comprises a second support member and the radiation source assembly is supported at its opposed ends by the first support member and the second support member.

16. The radiation source module defined in claim 15, the frame comprises a third support member interconnecting the first support member and the second support member.

17. The radiation source module defined in claim 1, wherein the power supply is disposed within a portion of the frame.

18. The radiation source module defined in claim 1, wherein the power supply is connected to an exterior of the frame.

19. A fluid treatment system comprising a radiation source module defined in claim 1.

20. A radiation source module comprising:
a frame having a first support member;
at least one radiation source assembly extending from and in engagement with the first support member;
a radiation source disposed in the radiation source assembly;
connection means for affixing the radiation source module in a fluid treatment system; and
a power supply connected to the frame and configured to be in contact with a fluid, wherein the power supply is integral with respect to the first support member.

21. A radiation source module comprising:
a frame having a first support member;
at least one radiation source assembly extending from and in engagement with the first support member;
a radiation source disposed in the radiation source assembly;
connection means for affixing the radiation source module in a fluid treatment system; and
a power supply connected to the frame and configured to be in contact with a fluid, wherein the power supply is connected to the connection means and a portion of the power supply is configured to contact a dielectric cooling liquid.

* * * * *